(12) United States Patent
Wang et al.

(10) Patent No.: US 12,233,225 B2
(45) Date of Patent: Feb. 25, 2025

(54) BLOOD COLLECTION DEVICES, SYSTEMS, AND METHODS FACILITATING BLOOD FLASHBACK

(71) Applicant: Becton, Dickinson and Company, Franklin Lakes, NJ (US)

(72) Inventors: Bin Wang, Irvine, CA (US); Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 17 days.

(21) Appl. No.: 18/092,798

(22) Filed: Jan. 3, 2023

(65) Prior Publication Data

US 2023/0141587 A1 May 11, 2023

Related U.S. Application Data

(63) Continuation of application No. 16/998,592, filed on Aug. 20, 2020, now Pat. No. 11,559,666.
(Continued)

(51) Int. Cl.
*A61M 25/06* (2006.01)
*A61M 25/00* (2006.01)
*A61M 5/31* (2006.01)

(52) U.S. Cl.
CPC .... *A61M 25/0693* (2013.01); *A61M 25/0097* (2013.01); *A61M 25/0606* (2013.01); *A61M 25/0625* (2013.01); *A61M 2005/3112* (2013.01)

(58) Field of Classification Search
CPC .......... A61M 25/0693; A61M 25/0097; A61M 25/0606; A61M 25/0625; A61M 39/10; A61M 2039/1077; A61B 5/150992
See application file for complete search history.

(56) References Cited

U.S. PATENT DOCUMENTS

| 4,193,400 A | 3/1980 | Loveless |
| 5,032,116 A | 7/1991 | Peterson et al. |

(Continued)

FOREIGN PATENT DOCUMENTS

| AU | 2016346887 A1 | 5/2018 |
| AU | 2019204246 A1 | 7/2019 |

(Continued)

*Primary Examiner* — William R Carpenter
*Assistant Examiner* — Robert F Allen
(74) *Attorney, Agent, or Firm* — Kirton McConkie; Whitney Blair; Kevin Stinger

(57) ABSTRACT

A catheter system may include a catheter adapter, a catheter extending distally from the distal end of the catheter adapter, and a needle hub coupled to the catheter adapter. The needle hub may be transparent, and a needle may be secured within the needle hub. The catheter system may also include a flow control plug coupled to the proximal end of the needle hub. In some embodiments, a flashback pathway may be disposed between an outer surface of the flow control plug and an inner surface of the needle hub. In some embodiments, the catheter system may include an inner barrel and an outer barrel, and the inner barrel and the needle hub may be configured to move proximally within the outer barrel to retract the needle. The flashback pathway may be disposed between an outer surface of the needle hub and an inner surface of the inner barrel.

6 Claims, 18 Drawing Sheets

Related U.S. Application Data

(60) Provisional application No. 62/901,631, filed on Sep. 17, 2019.

(56) References Cited

U.S. PATENT DOCUMENTS

| | | | |
|---|---|---|---|
| 5,496,281 A * | 3/1996 | Krebs | A61M 25/065 |
| | | | 604/168.01 |
| 5,800,399 A * | 9/1998 | Bogert | A61M 25/0014 |
| | | | 604/164.11 |
| 2004/0078003 A1 | 4/2004 | Smith et al. | |
| 2004/0210196 A1 | 10/2004 | Bush et al. | |
| 2007/0255221 A1 * | 11/2007 | Nakajima | A61M 25/0606 |
| | | | 604/168.01 |
| 2009/0227953 A1 | 9/2009 | Tan et al. | |
| 2010/0262038 A1 | 10/2010 | Tan et al. | |
| 2012/0016307 A1 * | 1/2012 | Burkholz | A61B 5/150916 |
| | | | 604/168.01 |
| 2012/0330187 A1 | 12/2012 | Tan et al. | |
| 2014/0257359 A1 | 9/2014 | Tegels et al. | |
| 2017/0120011 A1 * | 5/2017 | Burkholz | A61M 25/0637 |
| 2017/0120017 A1 * | 5/2017 | Burkholz | A61M 25/0606 |
| 2017/0274156 A1 * | 9/2017 | Isaacson | A61M 5/427 |
| 2018/0318557 A1 * | 11/2018 | Burkholz | A61M 39/10 |
| 2019/0247642 A1 | 8/2019 | Karthikeyan et al. | |
| 2020/0353220 A1 | 11/2020 | Burkholz et al. | |

FOREIGN PATENT DOCUMENTS

| | | | |
|---|---|---|---|
| CA | 3002665 A1 | | 5/2017 |
| CN | 103402429 A | | 11/2013 |
| CN | 106620941 A | | 5/2017 |
| CN | 206652048 U | | 11/2017 |
| EP | 3368125 A1 | | 9/2018 |
| JP | 2014073183 A | * | 4/2014 |
| JP | 2018531760 A | | 11/2018 |
| JP | 2020121173 A | | 8/2020 |
| SG | 11201802994 A | | 5/2018 |
| WO | 2017074682 A1 | | 5/2017 |

* cited by examiner

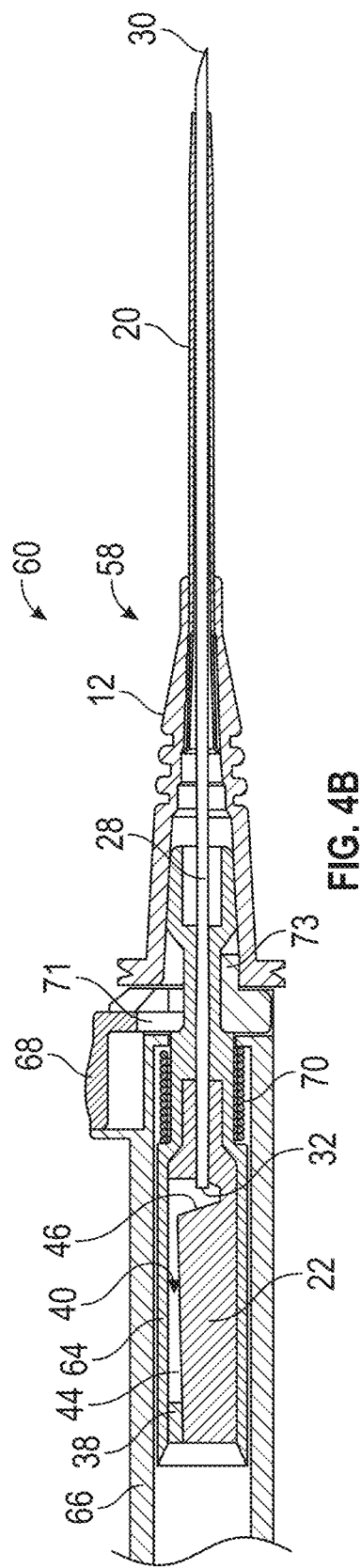

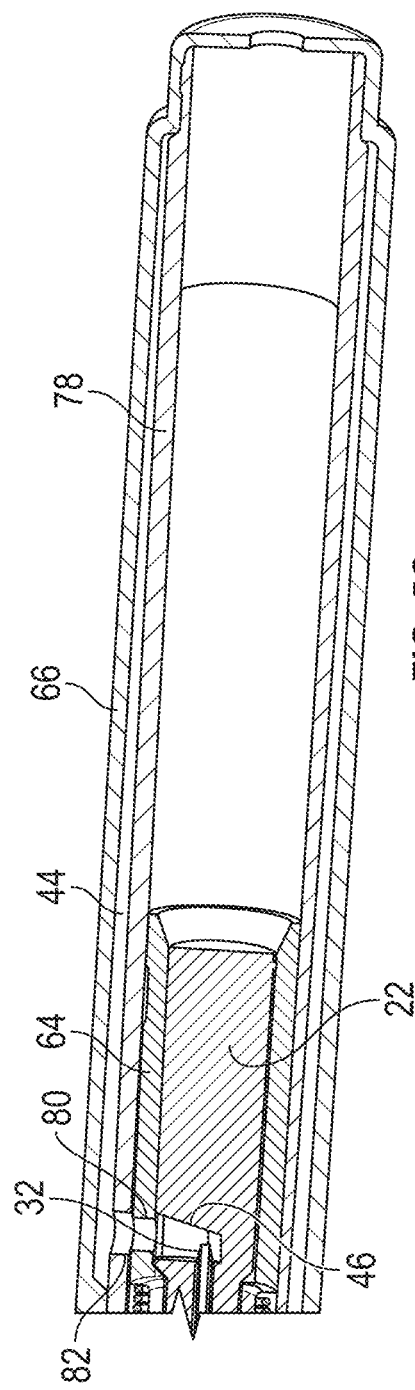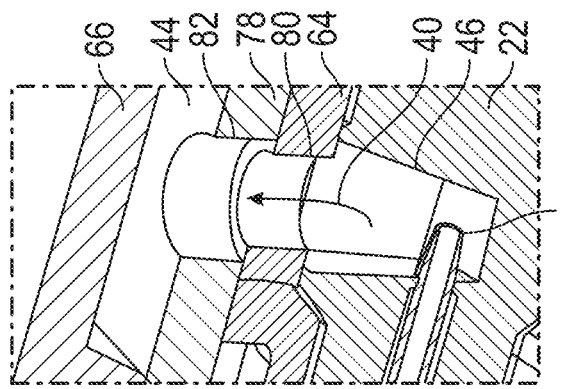

BLOOD COLLECTION DEVICES, SYSTEMS, AND METHODS FACILITATING BLOOD FLASHBACK

RELATED APPLICATIONS

This application is a continuation of U.S. patent application Ser. No. 16/998,592, filed Aug. 20, 2020, and entitled BLOOD COLLECTION DEVICES, SYSTEMS, AND METHODS FACILITATING BLOOD FLASHBACK, which claims the benefit of U.S. Provisional Patent Application No. 62/901,631, filed Sep. 17, 2019, and entitled BLOOD COLLECTION DEVICES, SYSTEMS, AND METHODS FACILITATING BLOOD FLASHBACK, which are incorporated herein in their entirety.

BACKGROUND

Intravenous catheters are commonly used for a variety of infusion therapies. For example, intravenous catheters may be used for infusing fluids, such as normal saline solution, various medicaments, and total parenteral nutrition, into a patient. Intravenous catheters may also be used for withdrawing blood from the patient.

Common types of intravenous catheter are peripheral IV catheters ("PIVCs"), peripherally inserted central catheters ("PICCs"), and midline catheters. Intravenous catheters may include "over-the needle" catheters, which may be mounted over a needle having a sharp distal tip. The sharp distal tip may be used to pierce skin and the vasculature of the patient. Insertion of the intravenous catheter into the vasculature may follow the piercing of the vasculature by the needle. The needle and the intravenous catheter are generally inserted at a shallow angle through the skin into the vasculature of the patient with a bevel of the needle facing up and away from the skin of the patient.

In order to verify proper placement of the introducer needle and/or the intravenous catheter in the vasculature, a user generally confirms that there is flashback of blood, which may be visible to the user. In some instances, the introducer needle may include a notch disposed towards a distal end of the introducer needle, and in response to the distal tip of the introducer needle being positioned within the vasculature, blood may flow proximally through a needle lumen, exit the needle lumen through the notch, and then travel proximally between an outer surface of the introducer needle and an inner surface of the intravenous catheter.

Accordingly, where the intravenous catheter is at least partially transparent, the user may visualize a small amount of blood "flashback" and thereby confirm placement of the intravenous catheter within the vasculature. Presence of a vasculature entrance indicator, such as flashback, may facilitate successful placement of intravenous catheters. Once placement of the introducer needle within the vasculature has been confirmed, the user may temporarily occlude flow in the vasculature and withdraw the introducer needle, leaving the intravenous catheter in place for future blood withdrawal and/or fluid infusion.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure generally relates to blood collection devices, systems, and methods to facilitate blood flashback. In some embodiments, a catheter system may include a catheter adapter which may include a distal end, a proximal end, and a lumen extending through the distal end and the proximal end. In some embodiments, the catheter system may include a catheter extending distally from the distal end of the catheter adapter. In some embodiments, the catheter system may include a needle hub, which may include a distal end and a proximal end. In some embodiments, the distal end of the needle hub may be coupled to the proximal end of the catheter adapter.

In some embodiments, the catheter system may include a peripheral intravenous catheter system, such as, for example, the BD NEXIVA™ Closed IV Catheter system, the BD CATHENA™ Catheter system, the BD VENFLON™ Pro Safely Shielded IV Catheter system, the BD NEOFLON™ IV Cannula system, the BD INSYTE™ AUTOGUARD™ BC Shielded IV Catheter system, or another suitable peripheral intravenous catheter system. In some embodiments, the catheter system may include a PICC system or a midline catheter system.

In some embodiments, the catheter system may include a needle, which may include a distal end and a proximal end. In some embodiments, the needle may include an introducer needle, which may include a sharp distal tip. In some embodiments, the needle may be secured within the needle hub. In some embodiments, the catheter system may include a flow control plug, which may be coupled to the proximal end of the needle hub. In some embodiments, the flow control plug may block a proximal opening of the needle hub such that blood does not exit the proximal opening of the needle hub. In some embodiments, the flow control plug may include one or more vents, which may include a porous membrane or microgrooves that may vent air while containing blood.

In some embodiments, the catheter system may include a flashback pathway disposed between an outer surface of the flow control plug and an inner surface of the needle hub. In some embodiments, the needle hub may be constructed of a clear or transparent material, which may facilitate observation blood within the flashback pathway. In some embodiments, the needle hub may include a lens, which may facilitate observation of blood within the flashback pathway. In some embodiments, the flow control plug may be constructed of a white material, which may provide a sharp contrast when blood flows into the flashback pathway.

In some embodiments, the outer surface of the flow control plug may include a channel. In some embodiments, the flashback pathway may extend through the channel between the channel and the inner surface of the needle hub. In some embodiments, the channel may provide a high area-to-volume ratio and may include a small height compared to its width. In some embodiments, a velocity of blood travelling within the channel may be between 1 mm/s and 2 mm/s. In some embodiments, a velocity of blood travelling within the channel may between 0.22 mm/s and 2 mm/s, which may create a continuous motion indicative of vein access in a real-time or near real-time manner. In some embodiments, it may take greater than 1 s for blood to move from one end of the channel to the other. For example, it may take between 5 s and 20 s for blood to move through the channel.

In some embodiments, the flashback pathway may provide an unobstructed, sharp-contrast visualization of a small volume of blood. In some embodiments, the catheter system may provide an effective signal for vein confirmation with a small amount of blood, such as approximately 10 mL. In some embodiments, the channel may be disposed on a top of the flow control plug, as illustrated, for example, in FIG. 1A, to ease visibility of the flashback pathway.

In some embodiments, the outer surface of the flow control plug may include a pocket proximate the channel. In some embodiments, the proximal end of the needle may be disposed within the pocket. In some embodiments, the pocket may be deeper than the channel. Blood travelling through the flashback pathway may be forced from the pocket to an outside of the flow control plug, which may improve visibility of the blood within the flashback pathway to the clinician.

In some embodiments, the channel may be formed by multiple side walls, which may extend from a bottom of the channel to the inner surface of the needle hub and may contact the inner surface of the needle hub. Thus, blood may be contained within the channel as it travels proximally through the channel. In some embodiments, the vent may be disposed proximate the channel, such as at a proximal end of the channel. In some embodiments, the vent may be disposed at an interface between the proximal end of the needle hub and the flow control plug.

In some embodiments, the distal end of the flow control plug may include a male luer. In some embodiments, the male luer may include a slip male luer or a threaded male luer. In some embodiments, a tip of the male luer may include a generally planar surface, which may extend across the tip such that a shape of the flashback pathway is generally semi-circular.

In some embodiments, the outer surface of the flow control plug may include multiple channels, and the flashback pathway may extend through the channels between the channels and the inner surface of the needle hub. In some embodiments, the outer surface of the flow control plug may include one or more grooves extending from the channels inwardly towards a longitudinal axis of the flow control plug. In some embodiments, a proximal end of each of the channels may be formed by a proximal wall. In some embodiments, the proximal wall may include one or more microgrooves configured to allow air but not blood to pass. In some embodiments, the proximal wall may interfere with an inner surface of the needle hub, which may prevent blood from exiting the proximal end of the channel.

In some embodiments, a catheter assembly of the catheter system may include the catheter adapter and the catheter. In some embodiments, a needle assembly of the catheter system may include one or more of the following: the needle hub, the needle, an inner barrel, and an outer barrel. In some embodiments, the inner barrel may surround the needle hub. In some embodiments, the needle hub may be secured within the inner barrel. In some embodiments, the flashback pathway may be disposed between an outer surface of the needle hub and an inner surface of the inner barrel. In some embodiments, the flow control plug may be constructed of a white material, which may provide a sharp contrast when blood flows into the flashback pathway.

In some embodiments, the outer barrel may surround the inner barrel. In some embodiments, the inner barrel and the needle hub may be configured to move proximally within the outer barrel to retract the needle. In some embodiments, the needle assembly may include a button and/or a spring. In some embodiments, the inner barrel and the needle hub may move proximally within the outer barrel in response to depression of the button and actuation of the spring.

In some embodiments, the needle hub may include a channel, and the flashback pathway may extend through the channel between the channel and the inner surface of the inner barrel. In some embodiments, the needle hub may include a pocket proximate the channel. In some embodiments, the proximal end of the needle may be disposed within the pocket. In some embodiments, the pocket may be deeper than the channel. In some embodiments, a proximal end of the channel may be formed by a proximal wall of the needle hub. In some embodiments, the proximal wall may include one or more microgrooves configured to allow air but not blood to pass. In some embodiments, the proximal wall may interfere with an inner surface of the inner barrel. In some embodiments, the inner surface of the inner barrel may include one or more alignment ridges. In some embodiments, the outer surface of the needle hub may include one or more other alignment ridges, which may contact the alignment ridges.

In some embodiments, the needle assembly may include a middle barrel. In some embodiments, the inner barrel may include a hole and/or the middle barrel may include a hole aligned with the hole of the inner barrel. In some embodiments, the flashback pathway may include the first hole and the second hole and may extend between an outer surface of the middle barrel and an inner surface of the outer barrel. In some embodiments, the pocket may be proximate the first hole. In some embodiments, the inner barrel and the needle hub may be configured to move proximally within the middle barrel to retract the needle. In some embodiments, the inner barrel and the needle hub may move proximally in response to depression of the button and actuation of the spring.

It is to be understood that both the foregoing general description and the following detailed description are examples and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 4B is a cross-sectional view of the catheter system of FIG. 4A, according to some embodiments;

FIG. 4C is an upper perspective view of an example needle hub of the catheter system of FIG. 4A, according to some embodiments;

FIG. 5C is a cross-sectional view of a proximal end of the catheter system of FIG. 5A, according to some embodiments;

FIG. 5D is an enlarged cross-sectional view of an example pocket of the catheter system of FIG. 5A, according to some embodiments;

DESCRIPTION OF EMBODIMENTS

Figure 1A:
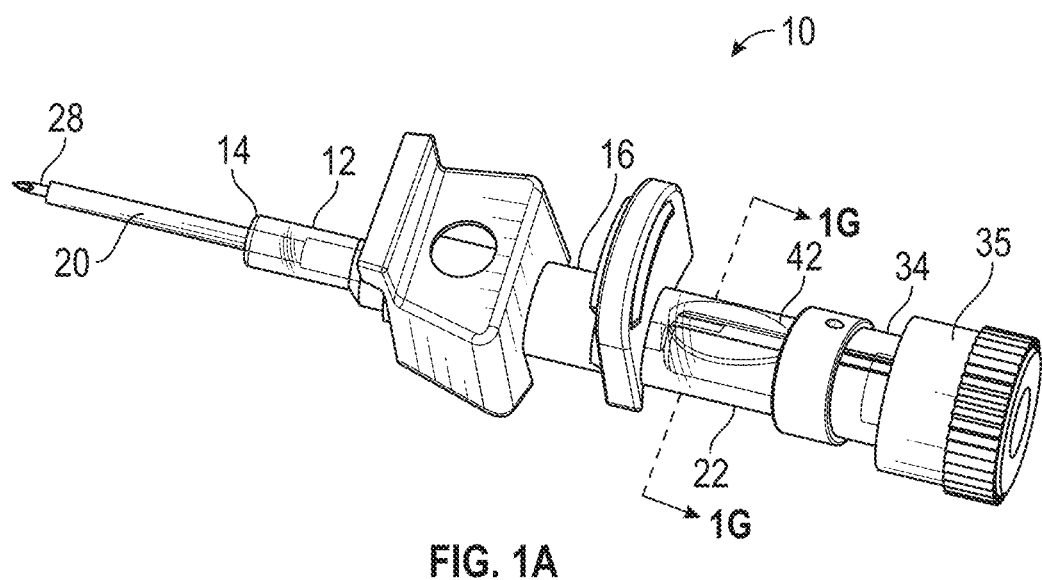
FIG. 1A is an upper perspective view of an example catheter system, according to some embodiments.
Figure 1B:
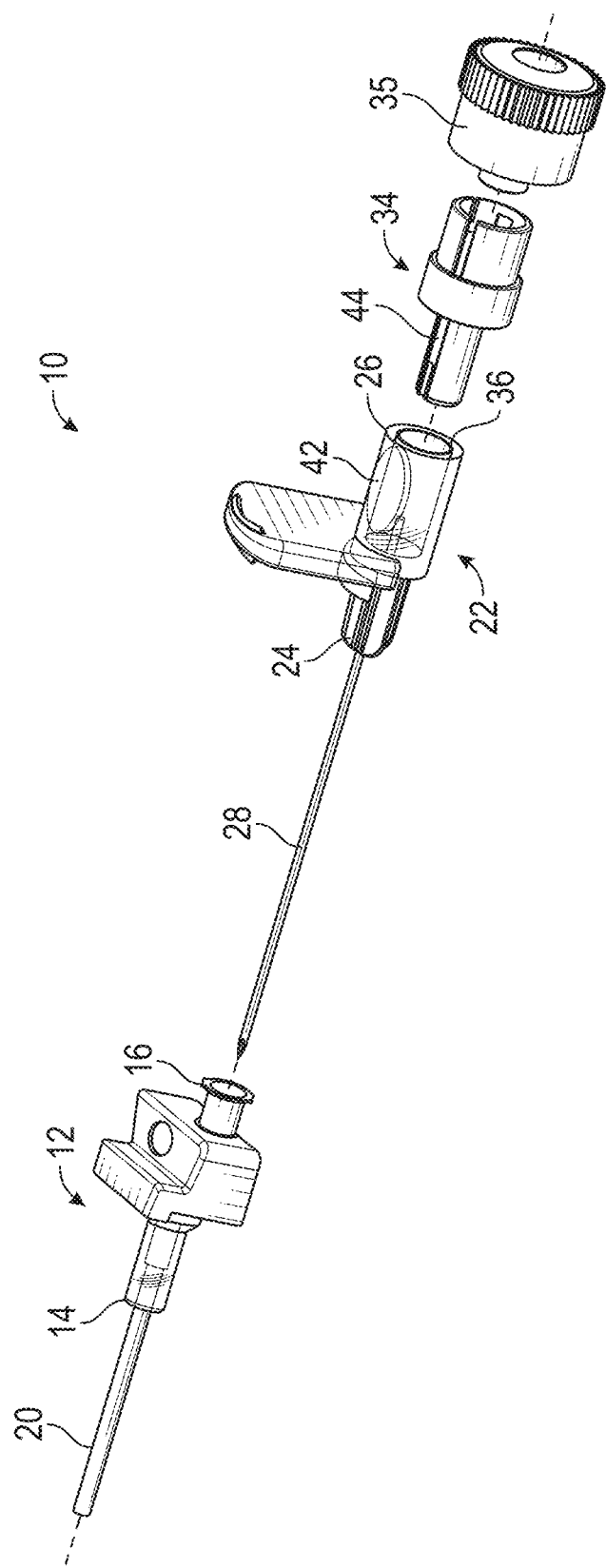
FIG. 1B is an exploded view of the catheter system of FIG. 1A, according to some embodiments.
Figure 1C:
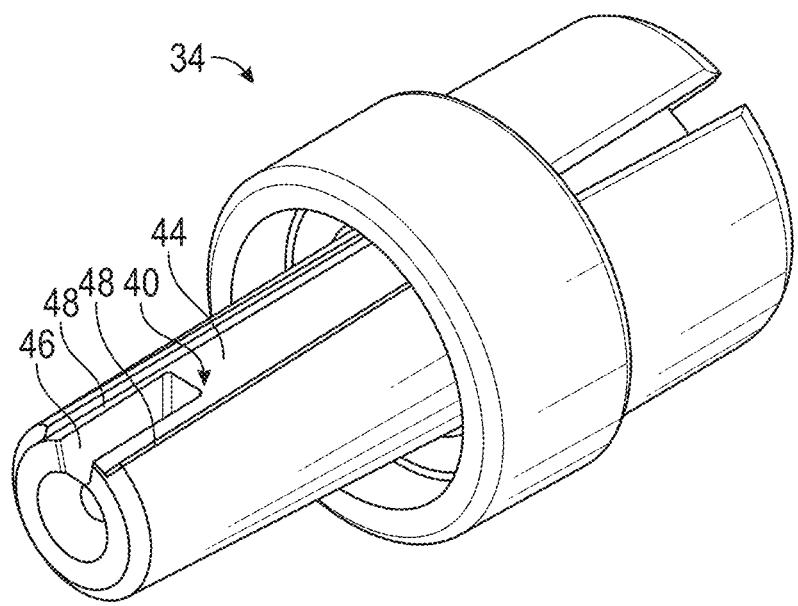
FIG. 1C is an upper perspective view of an example flow control plug, according to some embodiments.
Figure 1D:
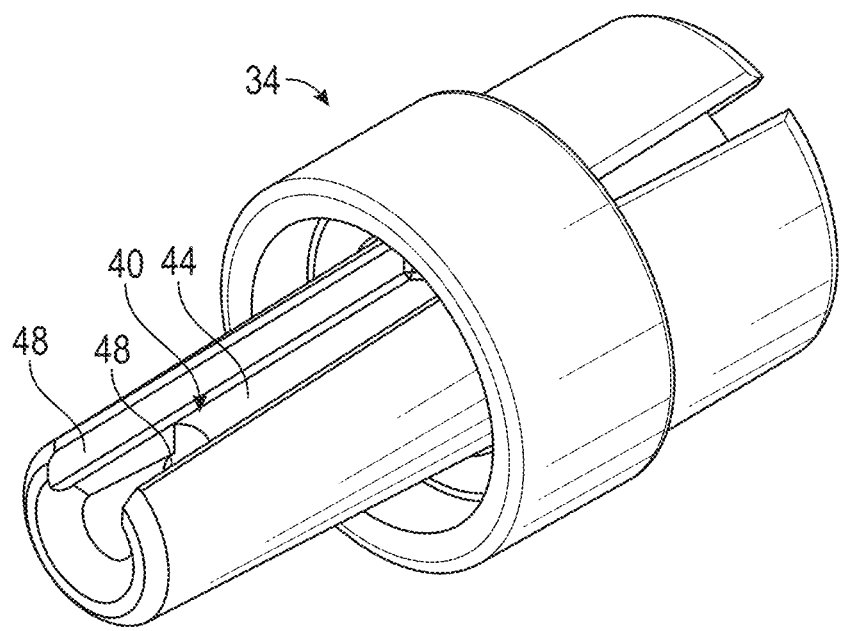
FIG. 1D is an upper perspective view of another example flow control plug, according to some embodiments.
Figure 1E:
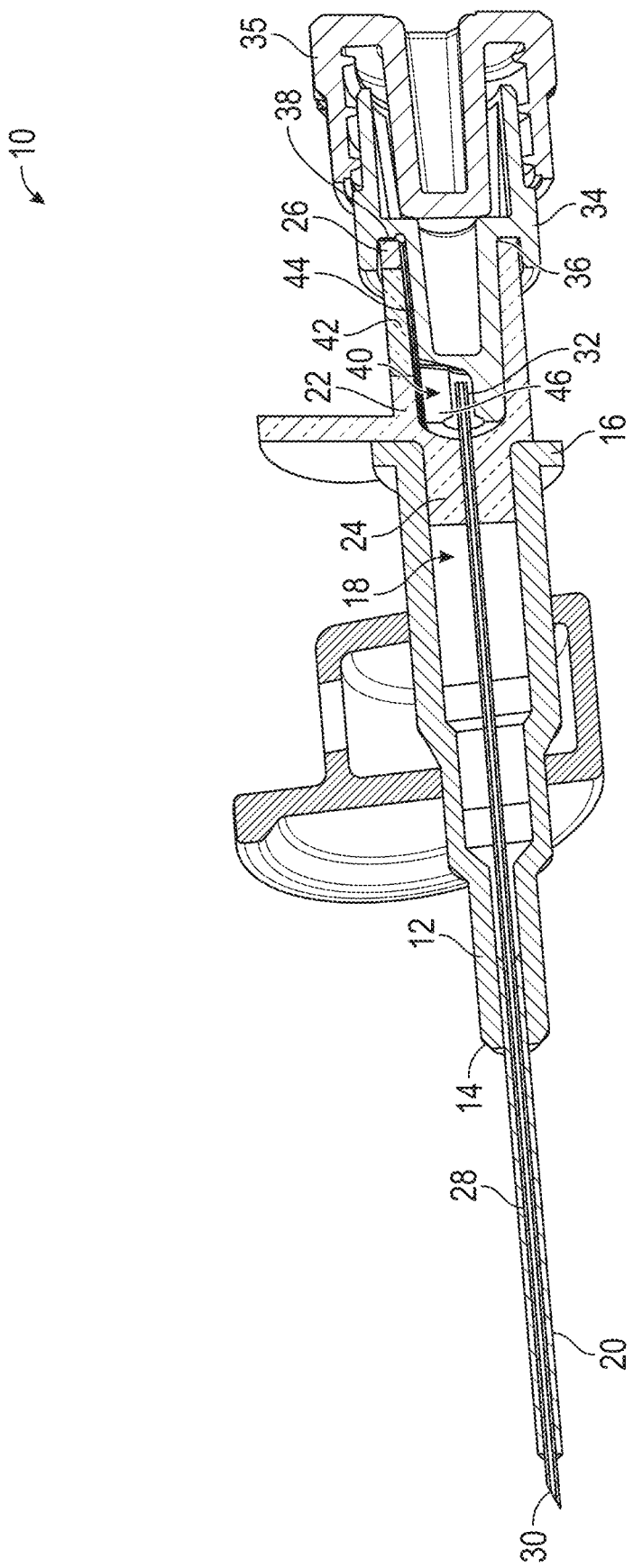
FIG. 1E is a cross-sectional view of the catheter system of FIG. 1A, according to some embodiments.
Figure 1F:
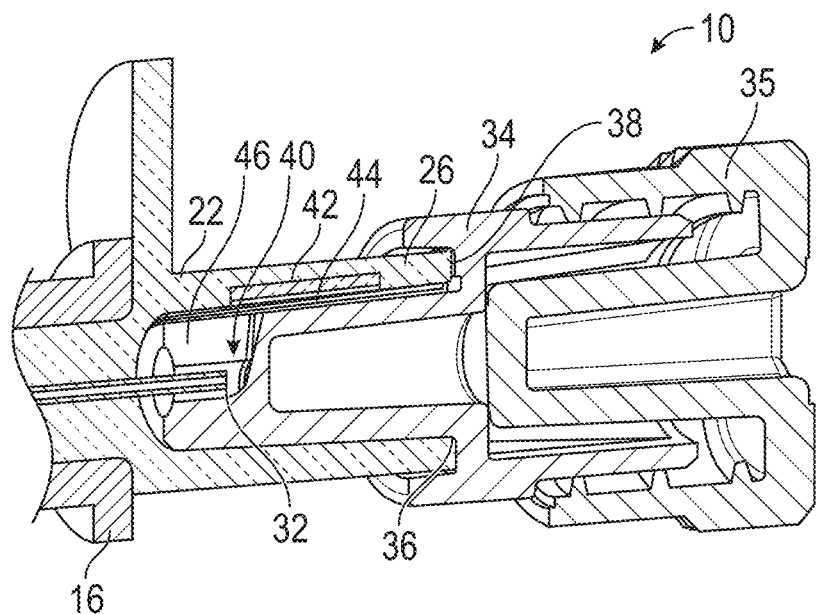
FIG. 1F is an enlarged cross-sectional view of a portion of the catheter system of FIG. 1A, according to some embodiments.
Figure 1G:
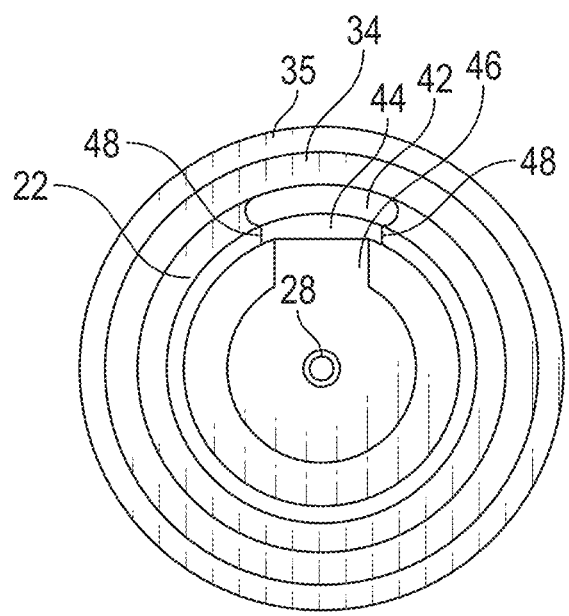
FIG. 1G is a cross-sectional view of the catheter system of FIG. 1A along the line 1G-1G of FIG. 1A, according to some embodiments.
Figure 2A:
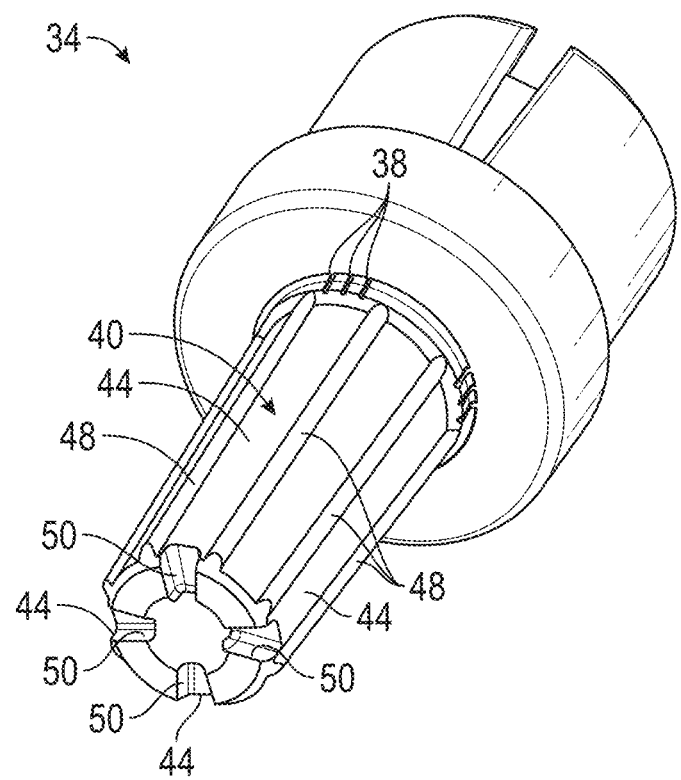
FIG. 2A is an upper perspective view of another example flow control plug, according to some embodiments.
Figure 2B:
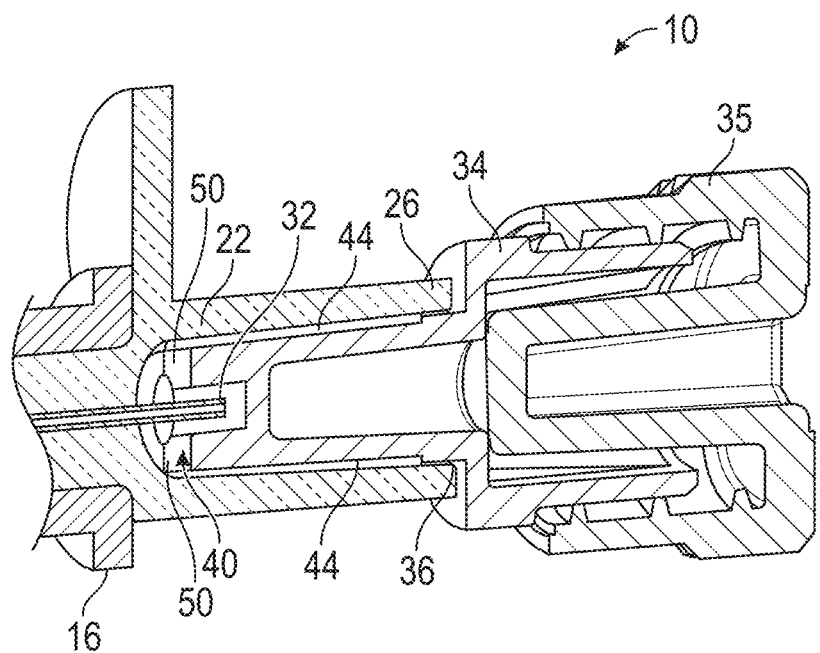
FIG. 2B is a cross-sectional view of the flow control plug of FIG. 2A coupled to the catheter system of FIG. 1A, according to some embodiments.
Figure 2C:
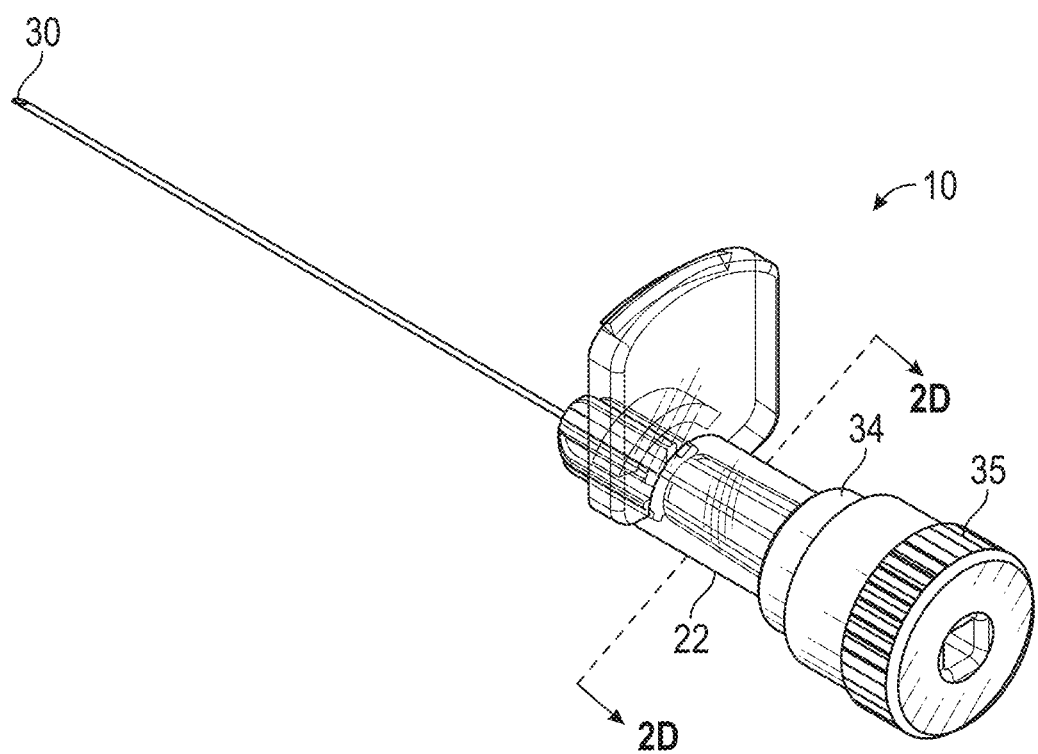
FIG. 2C is an upper perspective view if the flow control plug of FIG. 2A coupled to an example needle assembly, according to some embodiments.
Figure 2D:
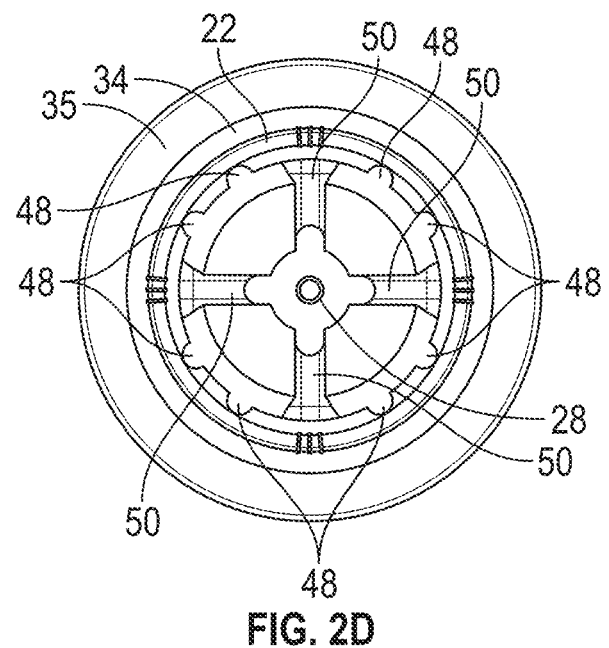
FIG. 2D is a transverse cross-sectional view along the line 2D-2D of FIG. 2C, according to some embodiments.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

Referring now to FIG. 1A-1G, in some embodiments, a catheter system 10 may include a catheter adapter 12 which may include a distal end 14, a proximal end 16, and a lumen 18 extending through the distal end 14 and the proximal end 16. In some embodiments, the catheter system 10 may include a catheter 20 extending distally from the distal end 14 of the catheter adapter 12. In some embodiments, the catheter system 10 may include a needle hub 22, which may include a distal end 24 and a proximal end 26. In some embodiments, the distal end 24 of the needle hub 22 may be coupled to the proximal end 16 of the catheter adapter 12.

In some embodiments, the catheter system 10 may include a peripheral intravenous catheter system, such as, for example, the BD NEXIVA™ Closed IV Catheter system, the BD CATHENA™ Catheter system, the BD VENFLON™ Pro Safely Shielded IV Catheter system, the BD NEOFLON™ IV Cannula system, the BD INSYTE™ AUTOGUARD™ BC Shielded IV Catheter system, or another suitable peripheral intravenous catheter system. In some embodiments, the catheter system 10 may include a PICC system or a midline catheter system.

In some embodiments, the catheter system 10 may include a needle 28 which may include a distal end 30 and a proximal end 32. In some embodiments, the needle 28 may include an introducer needle, which may include a sharp distal tip. In some embodiments, the needle 28 may be secured within the needle hub 22. In some embodiments, the catheter system 10 may include a flow control plug 34, which may be coupled to the proximal end 26 of the needle hub 22. In some embodiments, the flow control plug 34 may block a proximal opening 36 of the needle hub 22 such that blood does not exit the proximal opening 36 of the needle hub 22. In some embodiments, the flow control plug 34 may include one or more vents 38, which may include a porous membrane or a microgroove that may vent air while containing blood. In some embodiments, a cap 35 may be coupled to a proximal end of the flow control plug 34.

In some embodiments, the catheter system 10 may include a flashback pathway 40 disposed between an outer surface of the flow control plug 34 and an inner surface of the needle hub 22. In some embodiments, the needle hub 22 may be constructed of a clear or transparent material, which may facilitate observation blood within the flashback pathway 40. In some embodiments, the needle hub may include a lens 42, which may facilitate observation of blood within the flashback pathway 40. In some embodiments, the flow control plug 34 may be constructed of a white material, which may provide a sharp contrast when blood flows into the flashback pathway 40.

In some embodiments, the lens 42 may be disposed above a proximal end 32 of the needle 28. In some embodiments, the lens 42 may be integrated within the needle hub 22. In some embodiments, the lens 42 may be convex or another suitable shape. In some embodiments, an outer surface of the lens 42 may generally conform to a shape of an outer surface of the needle hub 22.

In some embodiments, the outer surface of the flow control plug 34 may include a channel 44. In some embodiments, the flashback pathway 40 may extend through the channel 44 between the channel 44 and the inner surface of the needle hub 22. In some embodiments, the channel 44 may provide a high area-to-volume ratio and may include a small height compared to its width. In some embodiments, a velocity of blood travelling within the channel 44 may be between 1 mm/s and 2 mm/s. In some embodiments, a velocity of blood travelling within the channel 44 may between 0.22 mm/s and 2 mm/s, which may create a continuous motion indicative of vein access in a real-time or near real-time manner. In some embodiments, it may take greater than 1 s for blood to move from one end of the channel 44 to the other. For example, it may take between 5 s and 20 s for blood to move through the channel 44. In some embodiments, the channel 44 may be axially aligned with a longitudinal axis of the catheter system 10.

In some embodiments, the flashback pathway 40 may provide an unobstructed, sharp-contrast visualization of a small volume of blood. In some embodiments, the catheter system 10 may provide an effective signal for vein confirmation with a small amount of blood, such as approximately 10 mL. In some embodiments, the channel 44 may be disposed on a top of the flow control plug 34, as illustrated, for example, in FIG. 1A, to ease visibility of the flashback pathway 40. A bevel of the sharp distal tip of the needle 28 may face toward a top of the catheter system 10 when the catheter system 10 is in an insertion position, ready for insertion into a patient, as illustrated, for example, in FIG. 1A.

In some embodiments, the outer surface of the flow control plug 34 may include a pocket 46 proximate the channel 44. In some embodiments, the proximal end 32 of the needle 28 may be disposed within the pocket 46. In some embodiments, the pocket 46 may be deeper than the channel 44. Blood travelling through the flashback pathway 40 may be forced from the pocket 46 to an outside of the flow control plug 34, which may improve visibility of the blood within the flashback pathway 40 to the clinician.

In some embodiments, the channel 44 may be formed by multiple side walls 48, which may extend from a bottom of the channel 44 to the inner surface of the needle hub 22 and may contact the inner surface of the needle hub 22. Thus, blood may be contained within the channel 44 as it travels proximally through the channel 44. In some embodiments, the vents 38 may be disposed proximate the channel 44, such as at a proximal end of the channel 44. In some embodiments, the vents 38 may be disposed at an interface between the proximal end 26 of the needle hub 22 and the flow control plug 34.

In some embodiments, the side walls 48 may include elongated ribs. In some embodiments, a height of the side walls 48 from a bottom of the channel 44 and/or a width of the channel 44 from one of the side walls 48 to the an opposite of the side walls 48 may increase with an increased gauge size of the catheter 20. For example, the flow control plug 34 illustrated in FIG. 1D may be used with a larger gauge catheter than the flow control plug 34 illustrated in FIG. 1C. As another example, the flow control plug 34 illustrated in FIG. 3A may be used with a larger gauge catheter than the flow control plug 34 illustrated in FIGS. 1C and 1D. In some embodiments, the distal end of the flow control plug 34 may include a male luer. In some embodiments, the male luer may include a slip male luer or a threaded male luer.

Referring now to FIGS. 2A-2D, in some embodiments, the outer surface of the flow control plug 34 may include multiple channels 44, and the flashback pathway 40 may extend through the channels 44 between the channels 44 and the inner surface of the needle hub 22. In some embodiments, a number of the channels 44 may vary. In some embodiments, the outer surface of the flow control plug 34 may include one or more grooves 50 extending from the channels 44 inwardly towards a longitudinal axis of the flow control plug 34. In some embodiments, the grooves 50 may be generally perpendicular to the channels 44.

In some embodiments, a proximal end of each of the channels 44 may be formed by a proximal wall 52. In some embodiments, the proximal wall 52 may include one or more microgrooves configured to allow air but not blood to pass. In some embodiments, the proximal wall 52 may interfere with an inner surface of the needle hub 22, which may prevent blood from exiting the proximal end of the channel 44.

In some embodiments, the needle hub 22 may be constructed of a clear or transparent material, which may facilitate observation blood within the flashback pathway 40. In some embodiments, the needle hub 22 may include one or more lenses, which may facilitate observation of blood within the flashback pathway 40. In some embodiments, the flow control plug 34 may be constructed of a white material, which may provide a sharp contrast when blood flows into the flashback pathway 40.

Figure 3A:
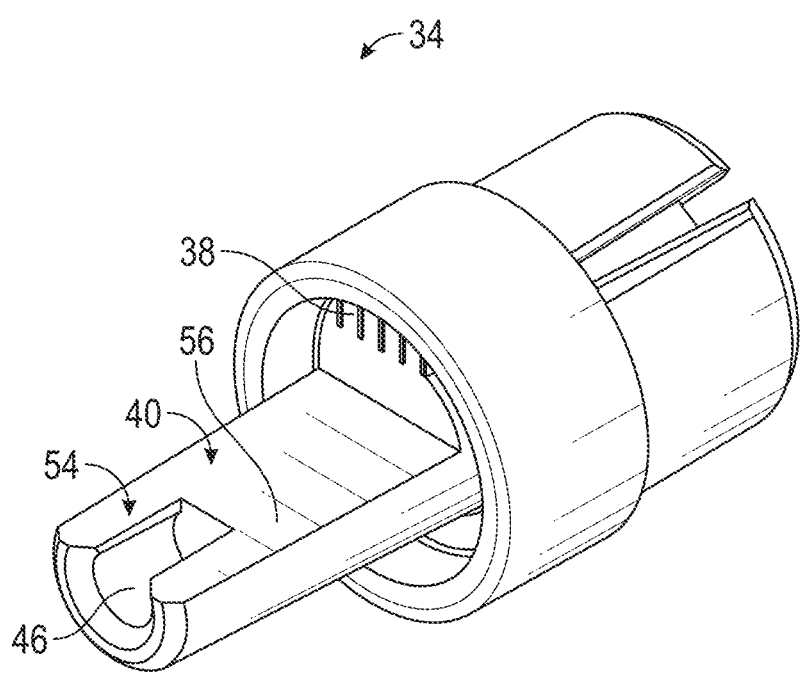
FIG. 3A is an upper perspective view of another example flow control plug, according to some embodiments.
Figure 3B:
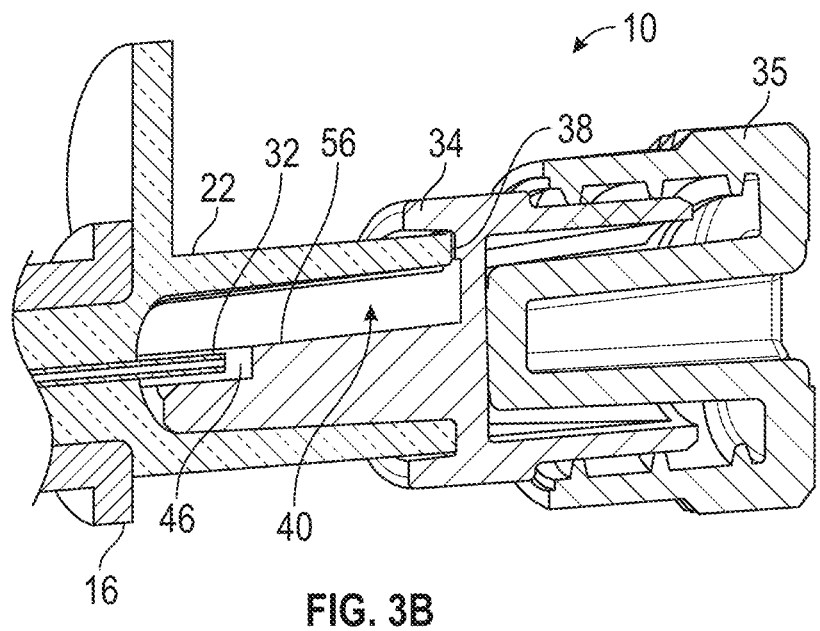
FIG. 3B is a cross-sectional view of the flow control plug of FIG. 3A coupled to the catheter system of FIG. 1A, according to some embodiments.
Figure 3C:
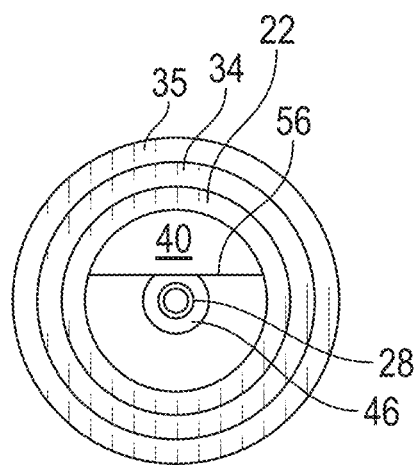
FIG. 3C is a transverse cross-sectional view of the flow control plug of FIG. 3A coupled to the catheter system of FIG. 1A, according to some embodiments.
Figure 4A:
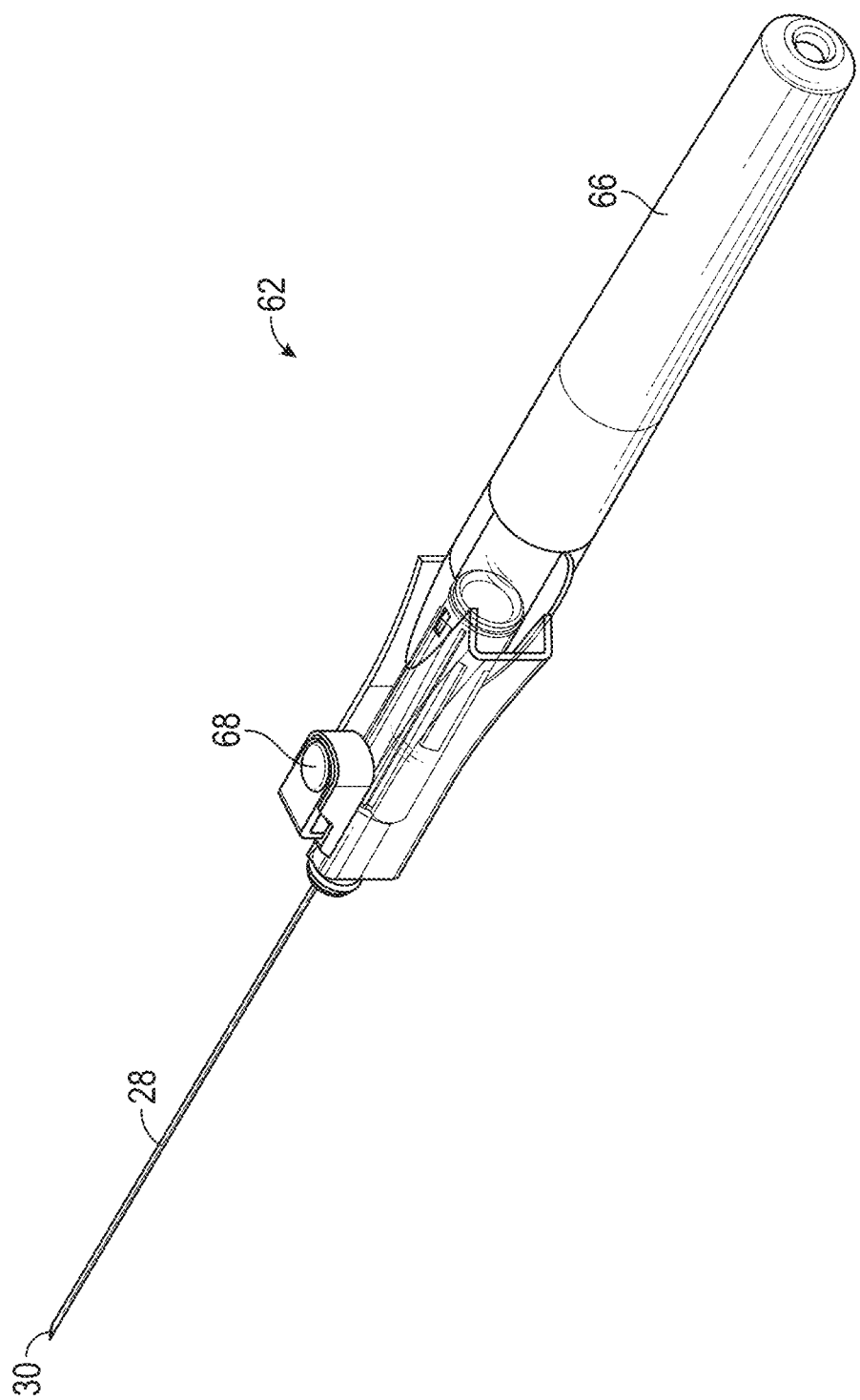
FIG. 4A is an upper perspective view of another catheter system, according to some embodiments.
Figure 4D:
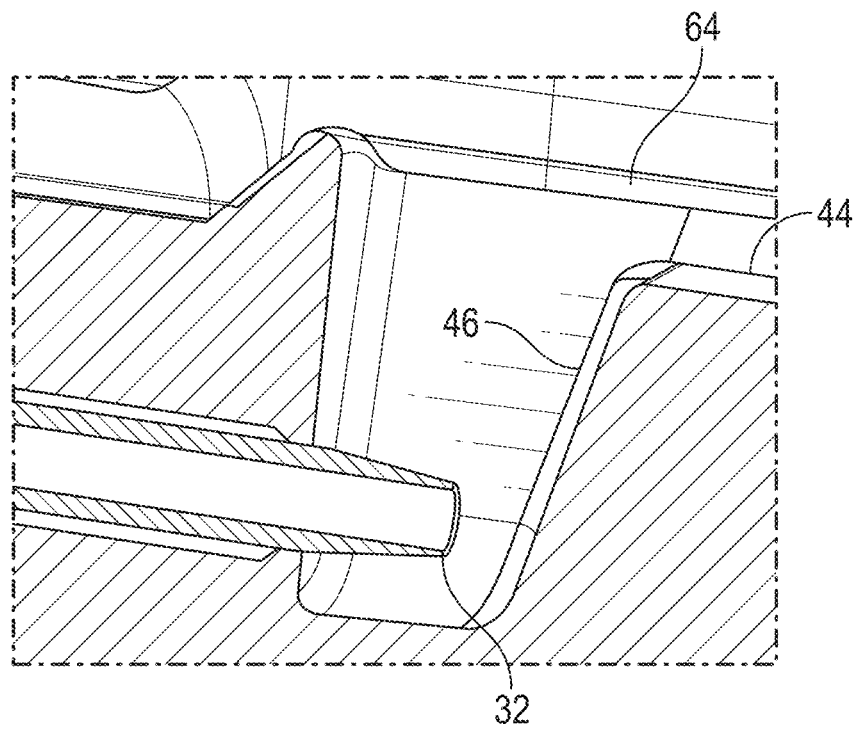
FIG. 4D is an enlarged cross-sectional view of an example pocket, according to some embodiments.
Figure 4E:
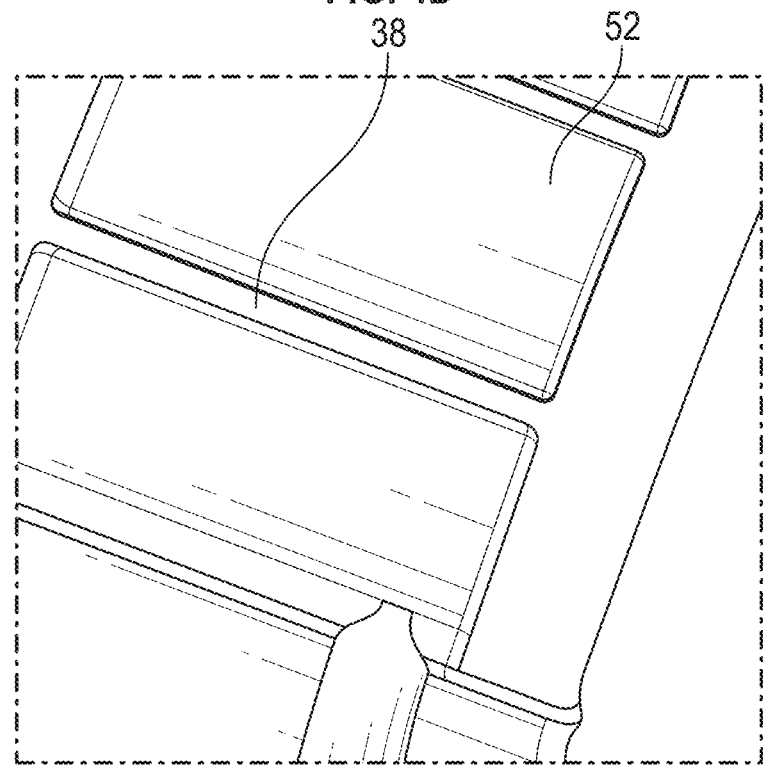
FIG. 4E is an enlarged upper perspective view of an example microgroove, according to some embodiments.
Figure 4F:
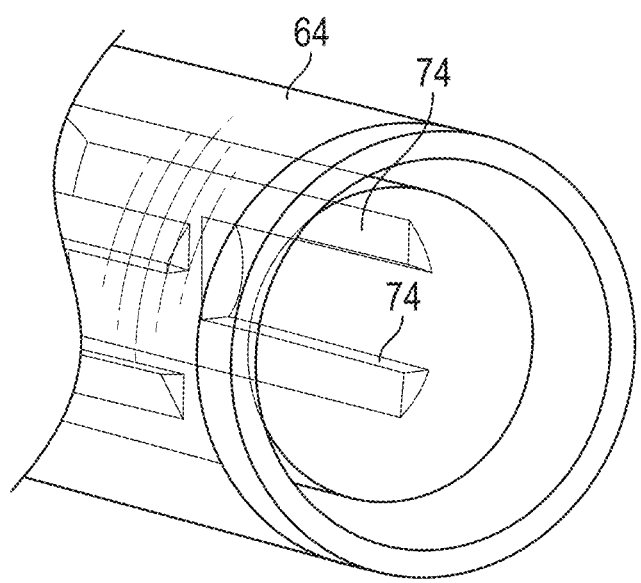
FIG. 4F is an upper perspective view of an example inner barrel, according to some embodiments.
Figure 5A:
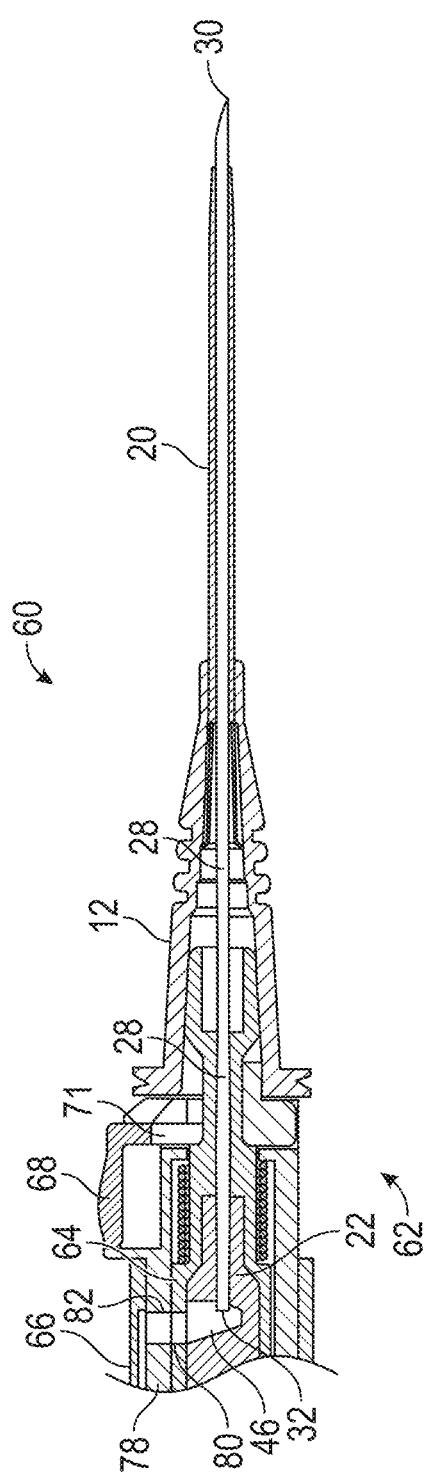
FIG. 5A is a cross-sectional view of another example catheter system, according to some embodiments.
Figure 5B:
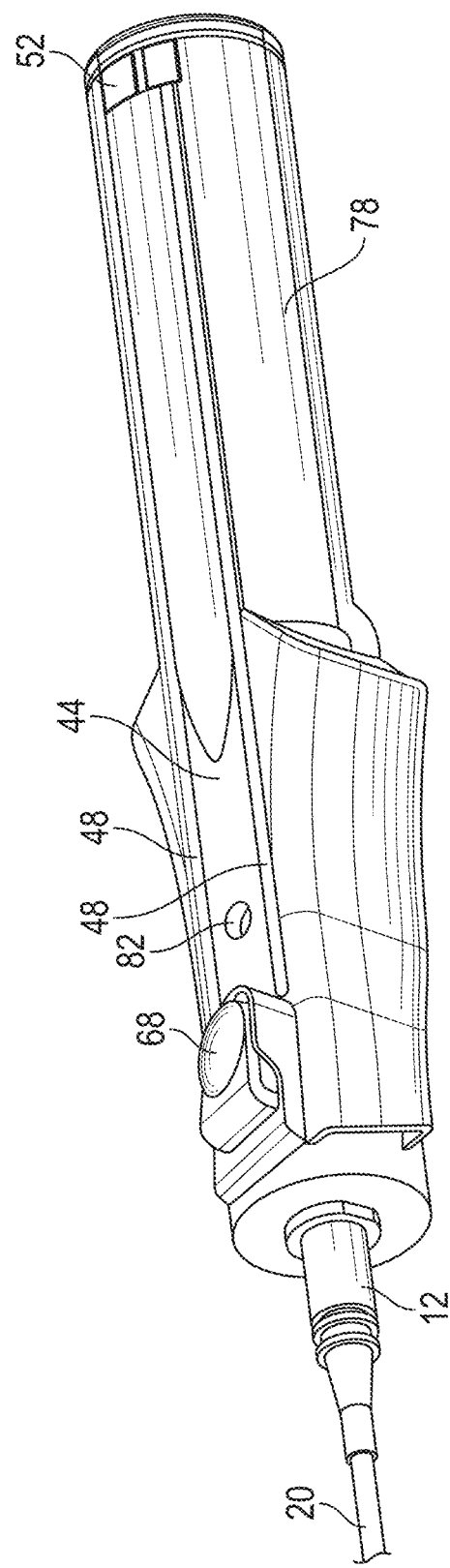
FIG. 5B is an upper perspective view of the catheter system of FIG. 5A, illustrating an example outer barrel removed, according to some embodiments.
Figure 5E:
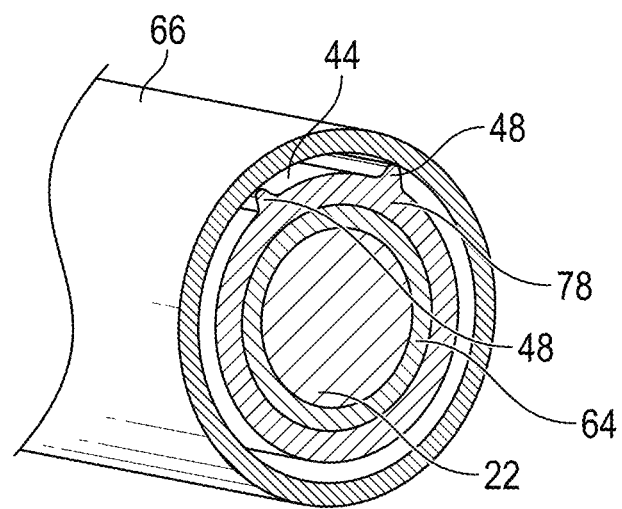
FIG. 5E is a transverse cross-sectional view of the catheter system of FIG. 5A, according to some embodiments.

Referring now to FIGS. 3A-3C, in some embodiments, a tip 54 of the male luer may include a generally planar surface 56, which may extend across the tip 54 such that a shape of the flashback pathway 40 is generally semi-circular. In some embodiments, the flow control plug 34 illustrated in FIG. 3A may be used with an 18 or 20 gauge catheter or another suitable size catheter.

Referring now to FIGS. 4A-4D, in some embodiments, a catheter assembly 58 of a catheter system 60 may include the catheter adapter 12 and the catheter 20. In some embodiments, the catheter system 60 may include or correspond to the catheter system 10 of one of more of FIGS. 1A-3C. In some embodiments, a needle assembly 62 of the catheter system 60 may include one or more of the following: the needle hub 22, the needle 28, an inner barrel 64, and an outer barrel 66. In some embodiments, the inner barrel 64 may surround the needle hub 22. In some embodiments, the needle hub 22 may be secured within the inner barrel 64. In some embodiments, the flashback pathway 40 may be disposed between an outer surface of the needle hub 22 and an inner surface of the inner barrel 64. In some embodiments, the flow control plug 34 may be constructed of a white material, which may provide a sharp contrast when blood flows into the flashback pathway 40.

In some embodiments, the outer barrel 66 may surround the inner barrel 64. In some embodiments, the inner barrel 64 and the needle hub 22 may be configured to move proximally within the outer barrel 66 to retract the needle 28. In some embodiments, the needle assembly 62 may include a button 68 and/or a spring 70. In some embodiments, the inner barrel 64 and the needle hub 22 may move proximally within the outer barrel 66 in response to depression of the button 68 and actuation of the spring 70. In some embodiments, a needle retraction mechanism of the catheter system 60 may operate similar to the BD INSYTE™ AUTO-GUARD™ BC Shielded IV Catheter System or another suitable catheter system.

In some embodiments, the inner barrel 64 may include a generally hour-glass shape so that its medial portion has a smaller diameter than either end. This shape facilitates engagement between an opening 71 in the button 68 and the inner barrel 64. In some embodiments, when the button 68 or activation latch is not depressed or is "up" in a non-activated position, a projection 73 may be located inside the catheter adapter 12. Thus, when the catheter 20 is still located on the needle 28 with the catheter adapter 12, the projection 73 may prevent the button 68 from being moved "down" into the activated position.

When the catheter 20 is moved off the needle 28 so the catheter adapter 12 is not adjacent to the projection 73, the button 68 may be moved "down," i.e. activated, because the catheter adapter 12 no longer interferes with the movement of the projection 73. In this position, the opening 71 is larger than a maximum diameter of inner barrel 64. The spring 70 can thus force the needle hub 22 and the inner barrel 64 to a proximal end of the outer barrel 66 and withdraw the distal end 30 of the needle 28 into the outer barrel 66. In some embodiments, the inner barrel 64 and the needle hub 22 may be integrally formed or monolithically formed as a single unit.

In some embodiments, the needle hub 22 may include a channel 44, and the flashback pathway 40 may extend through the channel 44 between the channel 44 and the inner surface of the inner barrel 64. In some embodiments, the needle hub 22 may include a pocket 46 proximate the channel 44. In some embodiments, the proximal end of the needle 28 may be disposed within the pocket 46. In some embodiments, the pocket 46 may be deeper than the channel 44. In some embodiments, a proximal end of the channel 44 may be formed by a proximal wall 52 of the needle hub 22. In some embodiments, the proximal wall 52 may include one or more vents, which may include a microgroove configured to allow air but not blood to pass. In some embodiments, the proximal wall 52 may interfere with an inner surface of the inner barrel 64. In some embodiments, the inner surface of the inner barrel 64 may include one or more alignment ridges 74. In some embodiments, the outer surface of the needle hub 22 may include one or more other alignment ridges 76, which may contact the alignment ridges 74 to facilitate orientation of the needle hub 22 with respect to the inner barrel 64.

Referring now to FIGS. 5A-5E, in some embodiments, the needle assembly 62 may include a middle barrel 78. In some embodiments, the inner barrel 64 may include a first hole 80 and/or the middle barrel 78 may include a second hole 82 aligned with the first hole 80 of the inner barrel 64. In some embodiments, the flashback pathway 40 may include the first hole 80 and the second hole 82 and may extend between an outer surface of the middle barrel 78 and an inner surface of the outer barrel 66.

In some embodiments, a pocket 46 may be proximate the first hole 80. In some embodiments, the inner barrel 64 and the needle hub 22 may be configured to move proximally within the middle barrel 78 to retract the needle 28. In some embodiments, the inner barrel 64 and the needle hub 22 may move proximally in response to depression of the button 68 and actuation of the spring 70.

In some embodiments, the outer surface of the middle barrel 78 may include a channel 44, and the flashback pathway 40 may extend through the channel 44 between the channel 44 and the inner surface of the inner barrel 64. In some embodiments, the needle hub 22 may include a pocket 46 proximate the channel 44. In some embodiments, the proximal end 32 of the needle 28 may be disposed within the pocket 46. In some embodiments, a proximal end of the channel 44 may be formed by a proximal wall 52 of the middle barrel 78. In some embodiments, the proximal wall 52 may include one or more vents, which may each include a microgroove configured to allow air but not blood to pass. In some embodiments, the proximal wall 52 may interfere with an inner surface of the outer barrel 66.

In some embodiments, the channel 44 may be formed by multiple side walls 48, which may extend from a bottom of the channel 44 to the inner surface of the outer barrel 66 and may contact the inner surface of the outer barrel 66. Thus, blood may be contained within the channel 44 as it travels proximally through the channel 44.

Figure 6A:
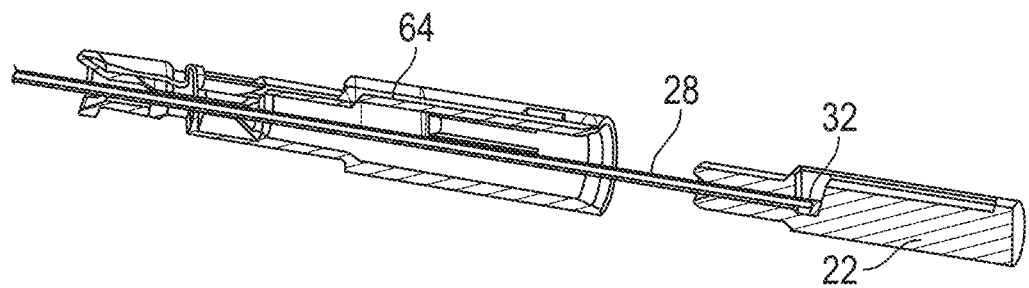
FIG. 6A is a cross-sectional view of an example needle hub being inserted into an example barrel, according to some embodiments.
Figure 6B:
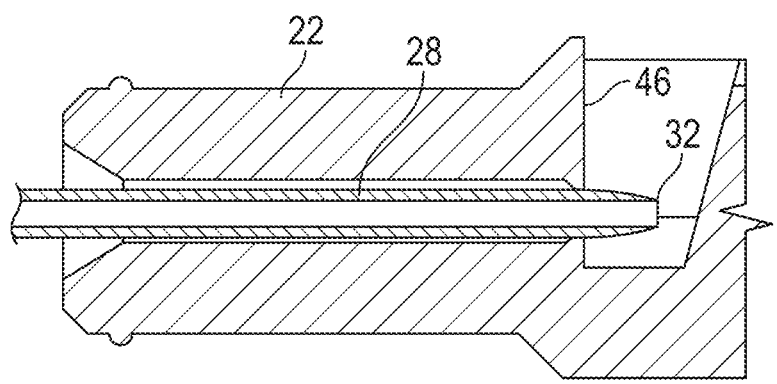
FIG. 6B is an enlarged cross-sectional view of a portion of the needle hub of FIG. 6A, according to some embodiments.

Referring now to FIGS. 6A-6B, the needle hub 22 is illustrated being inserted into the inner barrel 64 during assembly of a catheter system. The catheter system may include or correspond to the catheter system 60 of FIGS. 4A-4F and/or FIGS. 5A-5E. In some embodiments, the proximal end 32 of the needle 28 may contact and be secured within the needle hub 22, but a remaining portion of the needle 28 may not contact the needle hub 22 and/or any portion of the catheter system. In some embodiments, the proximal end 32 of the needle 28 may be pinched and/or glued within the needle hub 22, as illustrated, for example, in FIG. 6B.

Figure 6C:
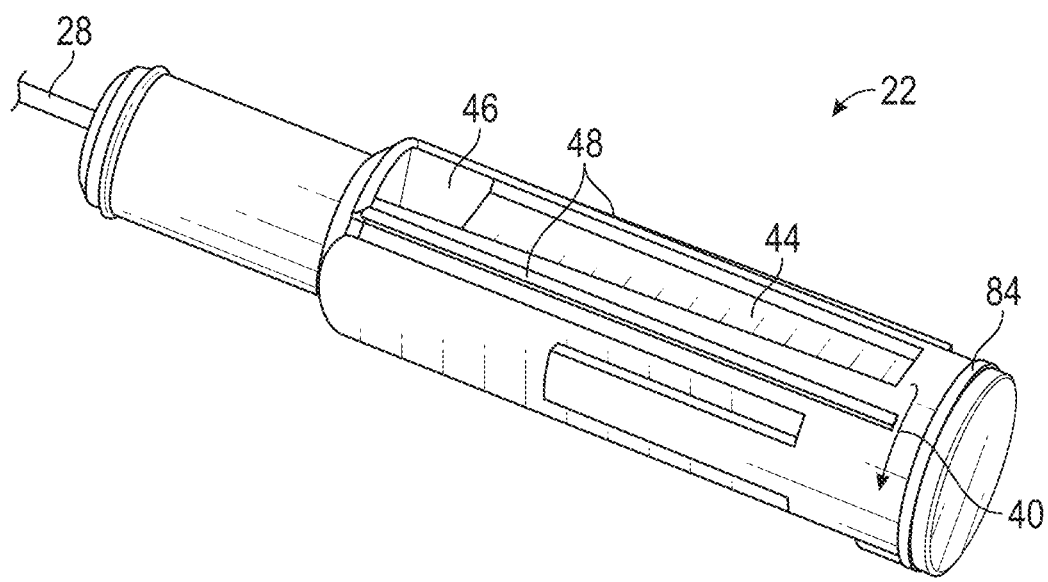
FIG. 6C is an upper perspective view of the needle hub of FIG. 6A, according to some embodiments.
Figure 6D:
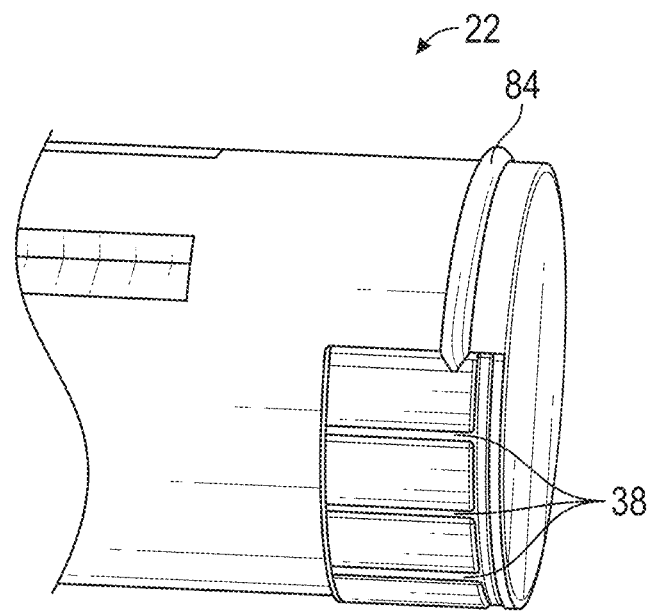
FIG. 6D is a lower perspective view of a portion of the needle hub of FIG. 6A, according to some embodiments.

Referring now to FIGS. 6C-6D, in some embodiments, the vents 38 may be disposed on a bottom of the needle hub 22, which may facilitate better fluid containment. In some embodiments, flashback may flow proximally through the channel 44 and then down one or more sides of the needle hub 22 to a location proximate the vents 38. In some embodiments, a proximal end of the needle hub 22 may include a seal 84, which may include a rib and/or may extend from one side of the vents 38 to the other.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

We claim:

1. A catheter system, comprising:
   a catheter assembly, comprising:
      a catheter adapter, comprising a distal end, a proximal end, and a lumen extending through the distal end and the proximal end; and
      a catheter extending distally from the distal end of the catheter adapter; and
   a needle assembly, comprising:
      a needle hub;
      a needle, comprising a distal end and a proximal end, wherein the needle is secured within the needle hub;
      an inner barrel surrounding the needle hub, wherein the needle hub is secured within the inner barrel, wherein the inner barrel comprises a first hole, wherein the needle hub is separately formed from the inner barrel and inserted into the inner barrel;
      a middle barrel surrounding the inner barrel, wherein the middle barrel comprises a second hole aligned with the first hole, wherein the needle hub comprises a pocket aligned with the first hole and the second hole, wherein the proximal end of the needle is disposed within the pocket;
      an outer barrel surrounding the middle barrel; and
      a flashback pathway comprising the pocket, the first hole, and the second hole and extending between an outer surface of the middle barrel and an inner surface of the outer barrel.

2. The catheter system of claim 1, wherein the middle barrel comprises a channel, wherein the channel is formed by a plurality of side walls that extend from a bottom of the channel to the inner surface of the outer barrel and contact the inner surface of the outer barrel.

3. The catheter system of claim 1, wherein the inner barrel and the needle hub are configured to move proximally within the middle barrel to retract the needle.

4. The catheter system of claim 3, wherein the needle assembly comprises a button and a spring, wherein the inner barrel and the needle hub move proximally in response to depression of the button and actuation of the spring.

5. The catheter system of claim 1, wherein a diameter of the pocket is generally similar to a diameter of the first hole.

6. The catheter system of claim 1, wherein the proximal end of the needle is aligned with the first hole and the second hole.

* * * * *